United States Patent [19]

Cardenas

[11] 4,001,307
[45] Jan. 4, 1977

[54] PREPARATION OF HALOESTERS FROM DIENES

[75] Inventor: Carlos G. Cardenas, Jacksonville, Fla.

[73] Assignee: SCM Corporation, New York, N.Y.

[22] Filed: May 10, 1973

[21] Appl. No.: 359,011

[52] U.S. Cl. .......................... 260/491; 260/497 R; 260/654 H
[51] Int. Cl.² ........................................ C07C 67/10
[58] Field of Search ........................ 260/491, 654 H

[56] References Cited
UNITED STATES PATENTS

| 287,249 | 4/1943 | Schmidt ........................ 260/654 H |
| 2,318,323 | 5/1943 | Mueller-Cunradi et al. ... 260/654 H |
| 2,366,667 | 1/1945 | Deebel ............................ 260/491 |
| 3,031,442 | 4/1962 | Webb ............................ 260/475 N |
| 3,110,740 | 11/1963 | Peer et al. ...................... 260/654 H |
| 3,293,286 | 12/1966 | Webb ............................ 260/475 N |
| 3,720,704 | 3/1973 | Sakomura et al. ................ 260/491 |

OTHER PUBLICATIONS
Hine, Physical Org. Chem., (1962), pp. 153–154.

*Primary Examiner*—Vivian Garner
*Attorney, Agent, or Firm*—Richard H. Thomas

[57] ABSTRACT

A process for the preparation of 4-halo-3-methylbut-2-enyl lower fatty acid esters from isoprene comprising the steps of halogenating isoprene in the presence of a dipolar aprotic solvent to produce a reaction mixture of which a predominant portion is 1,4-dihalo-2-methyl-2-butene, and esterifying said dihalo-butene under esterification reaction conditions with an alkali metal salt of a lower fatty acid. The amount of alkali metal salt is sufficient stoichiometrically to replace the halogen ion in the 1-position with the anion of said alkali metal salt, a substantial portion of the product of the esterification reaction being desired 4-halo-3-methylbut-2-enyl lower fatty acid ester.

8 Claims, No Drawings

PREPARATION OF HALOESTERS FROM DIENES

The present invention relates to the preparation of unsaturated haloesters, e.g., a chloroallylic ester, and preferably to an improved method for the preparation of such esters from dienes. A preferred form of the invention resides in the preparation of isoprene chloroacetate from isoprene.

The invention will be described with reference to isoprene and to the preparation of isoprene chloroacetate therefrom, but it will be apparent to those skilled in the art that the invention is applicable to the preparation of other halo lower fatty acid esters of isoprene.

BACKGROUND OF THE INVENTION

Prior application Ser. No. 246,939, filed Apr. 24, 1972, now abandoned by William Oroshnik, assigned to assignee of the present application, describes a new process for making Vitamin A carotenoid by-products of Vitamin A, and isomers thereof. One of the intermediates employed in the method of the application is isoprene chloroacetate (4-chloro-3-methylbut-2-enyl acetate) which has the structure

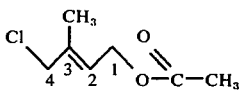

This compound may also be named 1-chloro-4-acetoxy-2-methyl-2-butene or 4-chloro-3-methyl-2-butene-1-yl acetate.

In addition to being useful in making Vitamin A and related products, the isoprene chloroacetate may also be a valuable intermediate in the synthesis of Vitamin E, in the synthesis of carotenoids and in the synthesis of many other terpenic and non-terpenic materials in which isoprene is a basic unit in the molecule.

The synthesis of isoprene chloroacetate is known and is reported in the *Journal of the American Chemical Society*, Volume 72, page 4608 (1950) in an article by W. Oroshnik and R. A. Mallory. The synthesis involved the treatment of isoprene with tert-butyl hypochlorite in the presence of a large excess of acetic acid. The method suffered from the disadvantages of a relatively low yield of chloroacetate, and of high cost. In addition, the hypochlorite is an unstable material rendering the synthesis difficult.

SUMMARY OF THE INVENTION

In accordance with the concepts of the present invention, an unsaturated haloester such as 4-chloro-3-methylbut-2-enyl acetate is prepared from a diene such as isoprene by first halogenating the diene in the presence of dipolar aprotic solvent such as N,N-dimethylformamide under conditions to form a high yield of a dihalo addition product, and then reacting the addition product with an alkali metal salt such as sodium acetate. These reaction steps preferably are carried out in sequence, the second reaction step of the addition product and alkali metal salt preferably being carried out in the presence of a catalyst such as triethylamine or a quaternary ammonium compound. Under preferred conditions about a 90% theoretical yield of the 1,4-dihalo-2-butene to haloester is achieved for a total improved yield of the haloester compared to the prior art, based on the weight of isoprene consumed.

The reaction of a halogen and diene are described in detail in copending application Ser. No. 350,755, filed Apr. 13, 1973, now U.S. Pat. No. 3,932,543, by Carlos G. Cardenas and Richard A. Von Genk, which application has been assigned to the assignee of the present application. An essential aspect of the invention of the copending application is the use of dipolar aprotic solvent in the halogenation reaction to give improved dihalide weight yields, e.g., 144% or better based on weight of diene consumed. A preferred solvent is dimethylformamide. Preferred reactant ratios are about one mole of solvent to about three moles of halogen and six moles of diene. The reaction may be carried out at ambient temperature. Preferred halogens are chlorine and bromine.

In one form of the invention, the solvent is present in sufficient amount to obtain an optimum yield of 1,4-dichloro-2-methyl-2-butene. This product is then reacted with sodium acetate in the presence of an amine catalyst to yield isoprene chloroacetate. The latter reaction is preferably carried out at a temperature preferably not substantially in excess of 100° C. and preferably in the presence of an acid scavenger such as sodium carbonate.

A portion of the dichloro product is 1,2-dichloro-2-methyl-3-butene. This compound can be isomerized to the 1,4 compound by reaction with CuCl or $CuCl_2$ in diethylene glycol or by other known methods to still further increase the yield of isoprene chloroacetate.

The reaction of the 1,4-dihalo addition product, such as 1,4-dichloro-2-methyl-2-butene, with an alkali metal salt, such as sodium acetate, actually produces four isomers of isoprene chloroacetate, the predominant isomers being the cis and trans forms 4-chloro-3-methylbut-2-enyl acetate. The less dominant isomers are the cis and trans forms of 4-chloro-2-methyl-2-butene-1-yl acetate, resulting from the replacement of the chlorine atom at the opposite end of the isoprene unit. The 4-chloro-3-methyl- and 4-chloro-2-methyl isomers can be separated from each other by known methods. In this regard, only the predominant cis and trans isomers of 4-chloro-3-methylbut-2-enyl acetate are useful in the process of the above-mentioned copending application Ser. No. 246,939.

The following examples illustrate the present invention.

EXAMPLE 1

This example is concerned with the chlorination of isoprene, carried out in the presence of a solvent in accordance with the concepts of copending application Ser. No. 350,755. The example illustrates the method for obtaining high yields of dichloride from isoprene, which in turn is necessary to obtain high yields of the isoprene chloroacetate based on the weight of isoprene consumed. Isoprene (204 grams, 3.0 moles) was stirred in a 500 ml. 3-neck round bottom flask at 25±2° C. in the dark in the presence of 36.5 grams (0.5 moles) of N,N-dimethylformamide (DMF). Chlorine (215 grams, 3.0 moles) was added via a fritted tube over a period of 145 minutes. Samples were taken during the course of the addition, were washed with water and were analyzed by gas chromatography giving the following ratios of primary products:

TABLE 1

| Time | Moles Cl₂ Added per mole Isoprene | Percent Substitution Products | Percent HCl Addition Products | Percent Desired Dichlorides | Percent Higher Mol. Wt. Cmpds. |
|---|---|---|---|---|---|
| 40 min. | 0.28 | 10.9 | — | 67.7 | — |
| 75 min. | 0.52 | 9.3 | — | 77.4 | — |
| 110 min. | 0.76 | 9.5 | 0.9 | 74.1 | 2.1 |
| 145 min. | 1.00 | 10.3 | 1.1 | 70.6 | 6.6 |

The weight yield of desired dichlorides, which were 1,2-dichloro-2-methyl-3-butene and cis- and trans-1,4-dichloro-2-methyl-2-butene, based on the weight of isoprene consumed, calculated to be about 144.5% after completion of addition. The substitution product was primarily 2-chloromethyl-1,3-butadiene, and the HCl addition products were primarily 1-chloro-3-methyl-2-butene and 2-chloro-2-methyl-3-butene.

By comparison, a similar test conducted employing no solvent resulted in much lower yields of the desired dichlorides, and higher amounts of the substitution and addition products. The weight yield of desired dichlorides based on the amount of isoprene consumed calculated to be about 54.3% after completion of addition, as compared to the above-mentioned yield of about 144.5% by the process of the present invention.

Other polar aprotic solvents which may successfully be employed in accordance with the present invention are N,N-dimethylacetamide (DMA), acetamide, N-methylpyrrolidine, hexamethyl phosphoramide (HMPA), dimethylsulfoxide (DMSO) and the corresponding thioamides where the oxygen atom is replaced by sulfur. Also a mixture of solvents may be employed, and the solvent system can include water in varying proportions.

In the chlorination reaction, an excess of aprotic solvent is not necessary, satisfactory yields being achieved with, by way of example, isoprene/DMF mole ratios of about 6:1 (about 0.16 moles of solvent per mole of diene). As a general rule, economics dictate that the least amount of solvent possible, without sacrificing yield, should be employed. However, ratios of below about 0.05 moles solvent per mole of diene may provide weight yields of dichloride addition products which are less than satisfactory. Increases in solvent/isoprene mole ratios above about 1:6 do not tend to give proportionate increases in yield. A preferred range for the dipolar aprotic solvent is about 0.1–0.6 moles per mole of diene. Nor is an excess of chlorine necessary. Satisfactory yields are obtained with about 50% conversion or consumption of isoprene (an isoprene/chloride mole of about 6:3), although higher conversions can be achieved without incurring losses. Temperatures below ambient appear to offer no advantage.

EXAMPLE 2

This example illustrates the preparation of isoprene chloroacetate in accordance with the concepts of the present invention. Isoprene (204 grams, 3.0 moles) was stirred in a 500 ml. 3-neck round bottom flask at 25±2° C. in the dark with 36.5 grams (0.5 moles) of N,N-dimethylformamide; and 106 grams (1.5 moles) of chlorine was added via a fritted tube over a period of 75 minutes. Upon completion of addition, the reaction mixture was poured into 500 ml. of water and was allowed to settle. The oil layer (299 g.) was separated, and isoprene was distilled off to a pot temperature of 100° C. The distillate (85 grams) contained 82 grams (95.94%) of isoprene by gas chromatographic analysis. The residue which weighed 197 grams contained the following:

TABLE 2

| Compound | Yield Grams |
|---|---|
| desired dichlorides | 151 |
| isoprene | 8.4 |
| substitution and HCl addition products | remainder |

The ratio of desired dichlorides was determind to be 25 parts of 1,2-dichloro-2-methyl-3-butene and 8.2 and 66.8 parts of cis and trans-1,4-dichloro-2-methyl-2-butene, respectively. The weight yield of desired dichlorides based on isoprene consumed was 133%.

The chloroacetate was then prepared by reacting 195 grams of the aforementioned residue in a 500 ml. 3-neck round bottom flask with 42.3 grams of sodium acetate in the presence of triethylamine (4.2 grams) and sodium carbonate (12.6 grams) at room temperature followed by stirring for one hour at 70° C. At the end of this period, heat was removed, 200 ml. of water were added, and stirring was continued for 5 minutes. The material was then allowed to settle and an organic layer (197 grams) was separated.

Gas chromatographic analysis of the separated layer showed 89.3 grams of dichlorides remaining indicating a consumption of 61.7 grams or 41% (61.7/151) of the original dichloride yield. Of the 41% portion, 46.1 grams or 74.7% (46.1/61.7) was cis-and trans -4-chloro-3-methylbut-2-enyl acetate, in the ratio of 12.5% cis- and 87.5% trans-, and 10.1 grams or 16.4% (10.1/61.7) was cis- and trans- 4-chloro-2-methyl-2-butene-1-yl acetate. This gave a total chloroacetate weight yield from dichlorides consumed of 91.1%, or 77.8% of theory. Separation of the two chloroacetate fractions is possible by known methods.

The chlorides remaining had the ratio of 1,2/cis-1,4/trans-1,4-dichloride of 41.1/4.3/54.6.

Instead of carrying out the preparation of the acetate in two independent steps separated by distillation, it is possible to carry out the chlorination and then the reaction with sodium acetate in the same pot following chlorination. In such case, both reactions would be carried out in the presence of a solvent at temperatures ranging from −100° to 300° C., optimum yields being obtained by chlorinating at about 25° C. and then increasing the temperature for reaction of the chlorination reaction products with sodium acetate. This will be illustrated by the following example.

EXAMPLE 3

Isoprene (204 grams, 3.0 mole) was stirred in a 500 ml 3-neck round bottom flask at 25±2° C. in the dark with 36.5 grams, N,N-dimethylformamide (0.5 moles) while 109.8 grams chlorine (1.5 moles) was added via a fritted tube over a period of 75 min. Upon completion of addition, 4.2 grams triethylamine, 42.3 grams sodium acetate and 12.6 grams sodium carbonate were added and the temperature was increased to 70° C. while distilling isoprene. The temperature was maintained at 70° C. for 1 hour during which 56.0 grams of distillate was obtained containing 97.20% or 54.4 grams of isoprene. After cooling to 50° C., 200 ml of H$_2$O was added to the residue and stirring was continued for 15 min. The material was then allowed to settle and an organic layer (222.8 grams) was separated and isoprene was distilled to a pot temperature of 100°. The distillate (15.4 grams) contained 95.47% or 14.7 grams of isoprene. Gas chromatographic analysis of the residue (203.0 grams) showed 119.4 grams of dichlorides remaining in a 1,2/cis-1,4/trans-1,4 ratio of 31.4/6.3/62.3, along with 24.8 grams of cis-and trans-4-chloro-3-methylbut-2-enyl acetate in a ratio of 14.4/85.6 comparable to the yield of Example 2.

In Examples 2 and 3, the sodium carbonate, although not usually required, functions as a scavenger to take up hydrochloric acid (HCl) formed. This can be accomplished by other weak inorganic bases, or in the one pot reaction of Example 3 with the use of DMF alone. The triethylamine functions as a catalyst, and can be replaced by quaternary ammonium compounds or lower or higher molecular weight amines as well as with similar compounds where the nitrogen is replaced by P, S, As, or Sb. Examples of suitable related catalysts in addition to triethylamine are benzyltriethylammonium chloride, mercaptans such as n-propyl mercaptan, alkyl sulfides such as allyl sulfide, and phosphines such as triphenyl phosphine. Some experience has shown that effective conversion can be achieved with no catalyst, although the use of a catalyst is preferred.

In place of the sodium acetate, other alkali metal salts of lower fatty acids can be employed.

It will also be apparent to those skilled in the art that the principles of the invention as exemplified by Examples 2 and 3 are useful in the making of halohydrins, haloethers, diesters, diols, diethers, diamines, haloamines, halonitriles, dinitriles and certain isoprene and other olefinic-containing polymers.

EXAMPLE 4

This example illustrates isomerization of the 1,2-dichloride to the 1,4-isomer. The isomerization is carried out with a catalyst such as CuCl or CuCl$_2$ preferably in the presence of a solvent. Improved yields were obtained with increased reaction time and temperature as shown in the following table:

TABLE 3

| Grams of 1,2-dichloride | Grams of Catalyst | Solvent | Conversion, % | | | | |
|---|---|---|---|---|---|---|---|
| | | | 1 hr 25° | 1 hr 40° | 2 hr 40° | 1 hr 70° | 2 hr 70° |
| 2.5 | 0.2 CuCl$_2$ | 20 ml Diethylene Glycol | 9 | 10 | 11 | 59 | 94 |
| 2.5 | 0.2 CuCl | " | 20 | 67 | 90 | 96 | 95 |

EXAMPLE 5

This example illustrates esterification without the use of sodium carbonate, and also illustrates other aspects of the invention. Four runs were made by placing the reactants in a 50 ml. flask and immersing the flask in a 70° C. oil bath and stirring magnetically. Samples were taken and washed with water, and the oil layer was analyzed by gas chromatography versus an internal standard.

TABLE 4

| | REACTANTS | | | |
|---|---|---|---|---|
| | 1 | 2 | 3 | 4 |
| Isoprene 1,4-dichloride (~90%) | 10.0 grams | 10.0 grams | 10.0 grams | 10.0 grams |
| triethylamine | .32 | .32 | | |
| sodium acetate | 3.2 | 3.2 | 3.2 | 3.2 |
| sodium carbonate | 1.0 | | | |
| benzyltriethyl ammonium chloride | | | | 0.73 |

The following Table 5 indicates that the conversion in run 3 without the presence of a catalyst was virtually zero. The table also shows that benzyltriethyl ammonium chloride gave a slower conversion but a somewhat better yield than triethylamine and that an acid scavenger is not essential for satisfactory yields.

TABLE 5

YIELD OF CHLOROACETATES BASED ON DICHLORIDES CONVERTED AS A FUNCTION OF TIME

| TIME | No. 1 | | No. 2 | | No. 3 | | No. 4 | |
|---|---|---|---|---|---|---|---|---|
| | Conv. % | Theory Yield % | Conv. % | Theory Yield % | Conv % | Theory Yield % | Conv % | Theory Yield % |
| 0.5 hr. | 48.0 | 73.6 | 46.9 | 87.2 | 0 | 0 | 33.2 | 74.9 |
| 1 hr. | * | * | 52.3 | 85.2 | 0 | 0 | 42.4 | 93.6 |
| 2 hr. | 56.5 | 76.4 | 54.0 | 85.0 | 0 | 0 | 54.2 | 90.3 |
| 4 hr. | 58.9 | 73.7 | 57.5 | 76.8 | 3.1 | 0 | 55.6 | 88.0 |
| 24 hr. | 60.7 | 67.8 | 56.5 | 75.8 | 0 | 0 | 55.1 | 82.3 |

*Unsatisfactory analysis

What is claimed is:
1. A process for the preparation of 4-halo-3-methylbut-2-enyl lower fatty acid esters from isoprene comprising the steps of;

a. halogenating isoprene in the presence of at least about 0.05 mols per mol of isoprene of a dipolar aprotic solvent selected from the group consisting of N,N-dimethylformamide, N,N-dimethylacetamide, acetamide, N-methylpyrrolidine, hexamethyl phosphoramide, and dimethylsulfoxide under halogenation conditions with elemental halogen to produce a reaction mixture a predominant portion of which is 1,4-dihalo-2-methyl-2-butene;

b. esterifying the reaction mixture of step (a) in an esterification reaction under esterification reaction conditions with an alkali metal salt of a lower fatty acid, the esterification reaction being carried out in the presence of a catalyst consisting essentially of an amine or phosphine at a temperature in the range of about −100° to 300° C, the amount of alkali metal salt employed being the amount stoichiometrically necessary to replace the halogen ion in the 1-position with the anion of said alkali metal salt to produce a product mixture of which a predominant portion is the desired 4-halo-3-methylbut-2-enyl lower fatty acid ester.

2. The process of claim 1 wherein said alkali metal salt is sodium acetate and said elemental halogen is chlorine, the resultant fatty acid ester being isoprene chloroacetate (4-chloro-3-methylbut-2-enyl acetate).

3. The process of claim 1 wherein the esterification reaction is carried out in the presence of an amine catalyst.

4. The process of claim 1 wherein the halogenation of isoprene is carried out at about 25° C., the reaction with sodium acetate being carried out at about 70° C.

5. The process of claim 1 wherein said reaction steps are carried out in a single reaction pot.

6. The process of claim 1 wherein the reaction of the 1,4-dihalo portion of the reaction product and sodium acetate is carried out in the presence of triethylamine.

7. The process of claim 6 wherein said halogen is chlorine, and a portion of said reaction product is 1,2-dichloro-2-methyl-3-butene further including the step of isomerizing said 1,2-dichloro - 2-methyl-3-butene to 1,4-dichloro-2-methyl-2-butene.

8. The process of claim 7 wherein the isomerization of the 1,2-dichloro-2-methyl-3-butene is carried out simultaneously with the esterification reaction or with the chlorination reaction, or both.

* * * * *